United States Patent [19]
Förster

[11] Patent Number: 4,482,318
[45] Date of Patent: Nov. 13, 1984

[54] ORTHODONTIC SPREADER

[75] Inventor: Rolf Förster, Pforzheim, Fed. Rep. of Germany

[73] Assignee: Bernhard Forster GmbH, Pforzheim, Fed. Rep. of Germany

[21] Appl. No.: 475,351

[22] Filed: Mar. 14, 1983

[30] Foreign Application Priority Data

Apr. 8, 1982 [DE] Fed. Rep. of Germany ... 8210086[U]
Jan. 20, 1983 [DE] Fed. Rep. of Germany ....... 3301753

[51] Int. Cl.$^3$ .............................................. A61C 3/00
[52] U.S. Cl. ........................................................ 433/7
[58] Field of Search ................................ 433/7, 18, 24

[56] References Cited

U.S. PATENT DOCUMENTS

| | | | |
|---|---|---|---|
| 3,800,420 | 4/1974 | Ouaknine | 433/7 |
| 3,835,540 | 9/1974 | Biederman | 433/7 |
| 3,921,294 | 11/1975 | Wallshein | 433/7 |
| 4,045,871 | 9/1977 | Nelson | 433/7 |
| 4,107,843 | 8/1978 | Spino et al. | 433/7 |
| 4,347,054 | 8/1982 | Kraus et al. | 433/7 |
| 4,379,693 | 4/1983 | Wallshein | 433/7 |

FOREIGN PATENT DOCUMENTS

| | | | |
|---|---|---|---|
| 556968 | 5/1957 | Belgium | 433/7 |
| 824832 | 11/1951 | Fed. Rep. of Germany | 433/7 |
| 2722611 | 11/1978 | Fed. Rep. of Germany | 433/7 |

Primary Examiner—John J. Wilson
Attorney, Agent, or Firm—Balogh, Osann, Kramer, Dvorak, Genova & Traub

[57] ABSTRACT

This invention relates to an orthodontic spreader, particularly for correcting the positions of molars in the upper jaw, and comprises pressure-transmitting nuts for applying force at points which are as close as possible to the center of resistance. The spreader is capable of applying a high pressure and has a large spreading capacity and is as convenient as possible for the patient. The actuating screw for moving the pressure-transmitting nuts in opposite directions comprises an actuating portion, which is disposed between said pressure-transmitting nuts. Guide rods are slidably mounted in both pressure-transmitting nuts and carry stops which axially restrain said guide rods.

13 Claims, 7 Drawing Figures

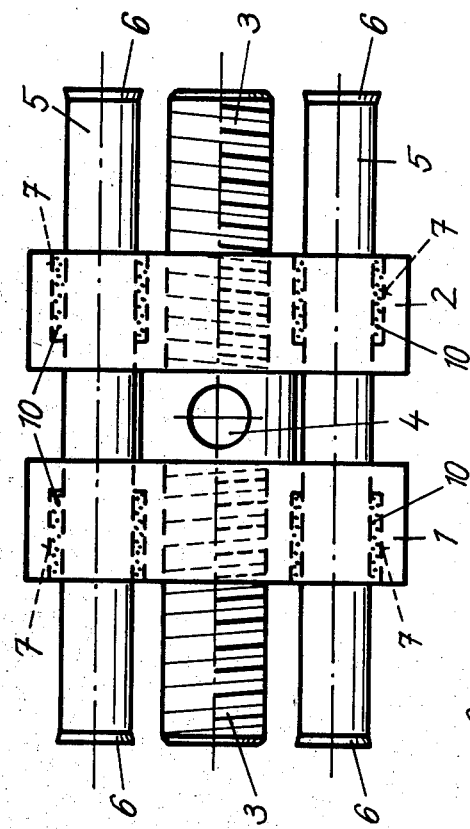
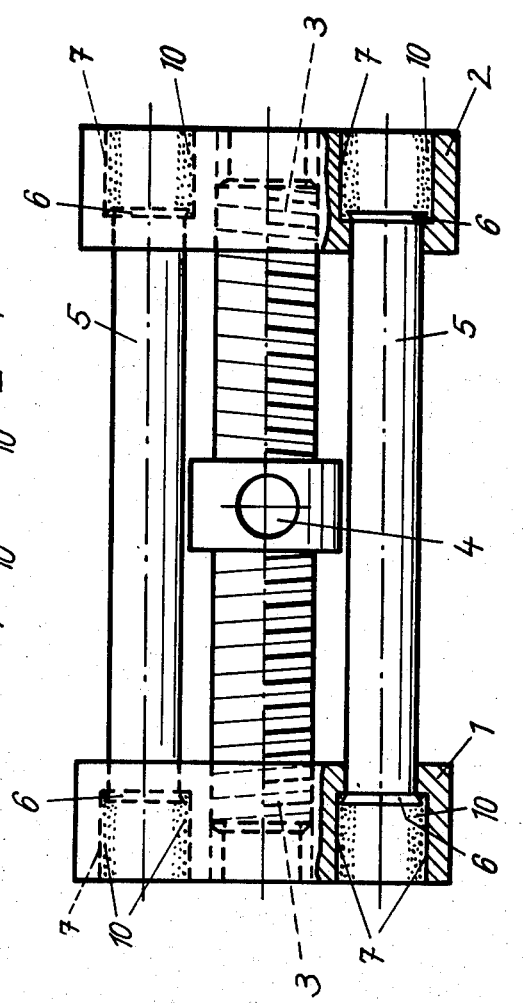
Fig. 1
Fig. 2

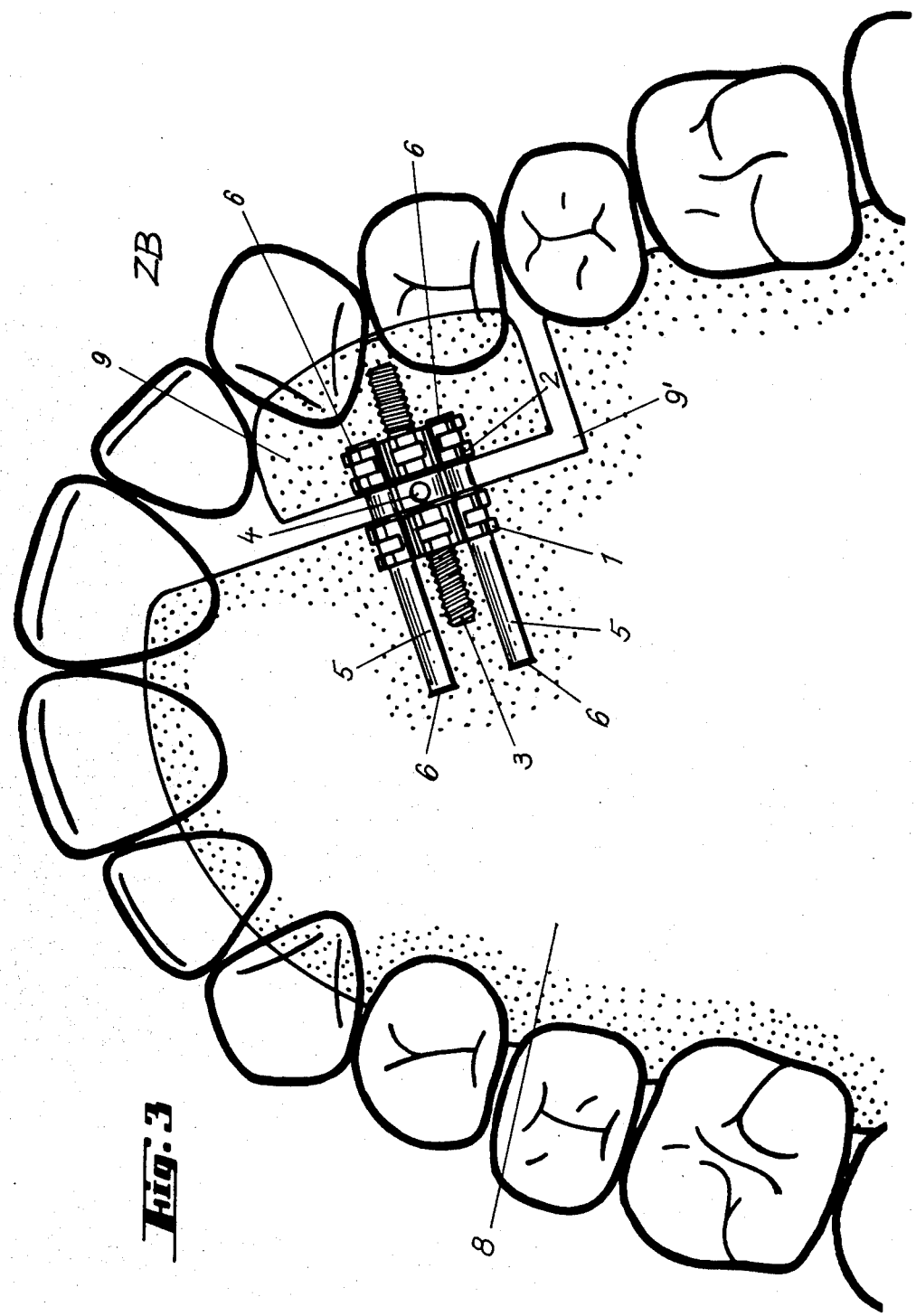

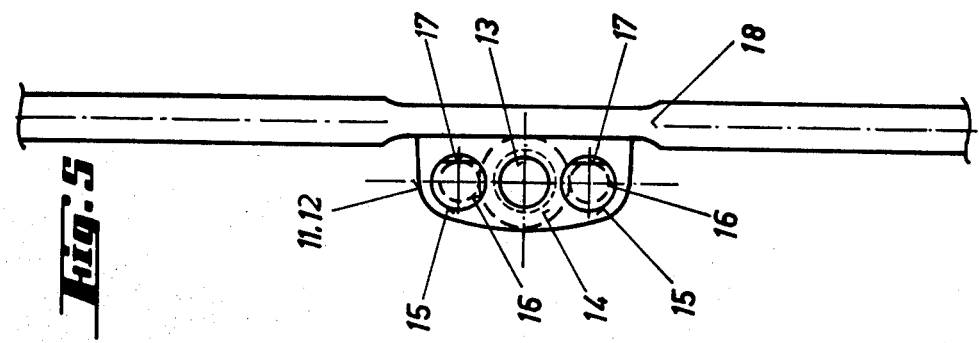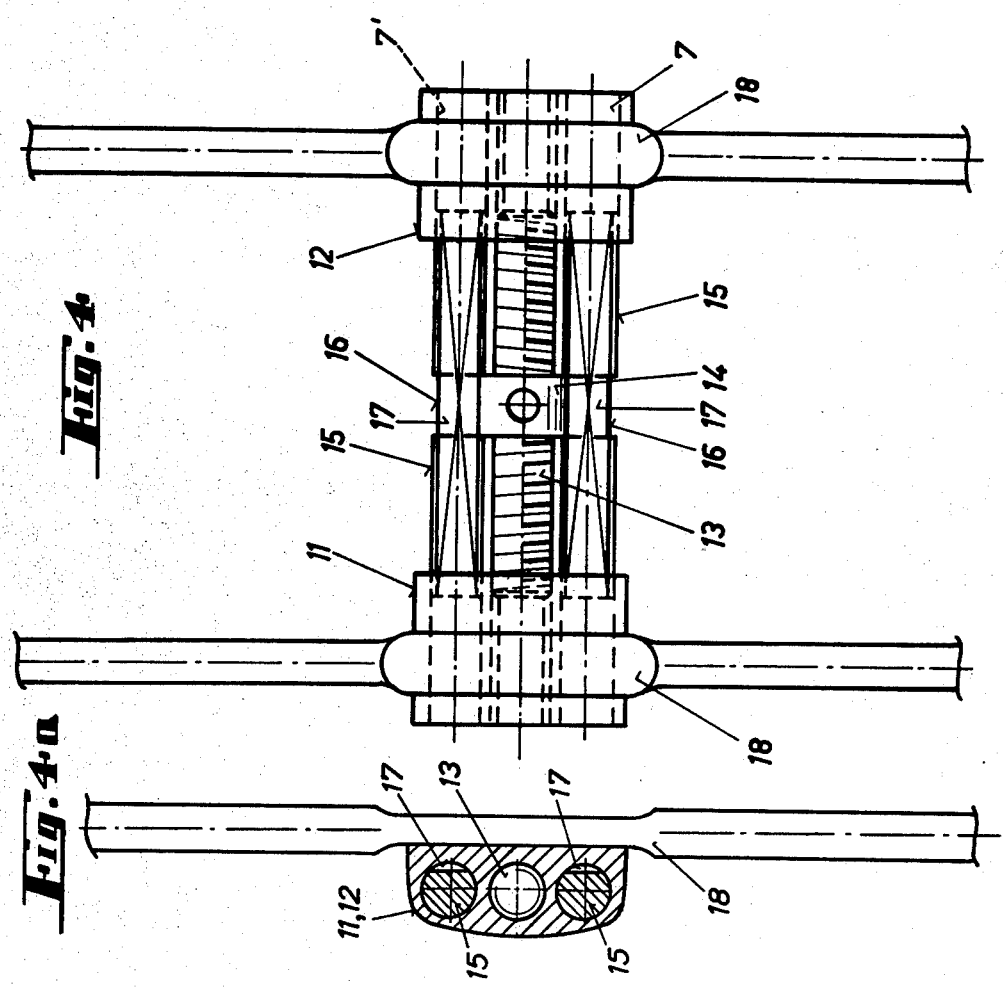

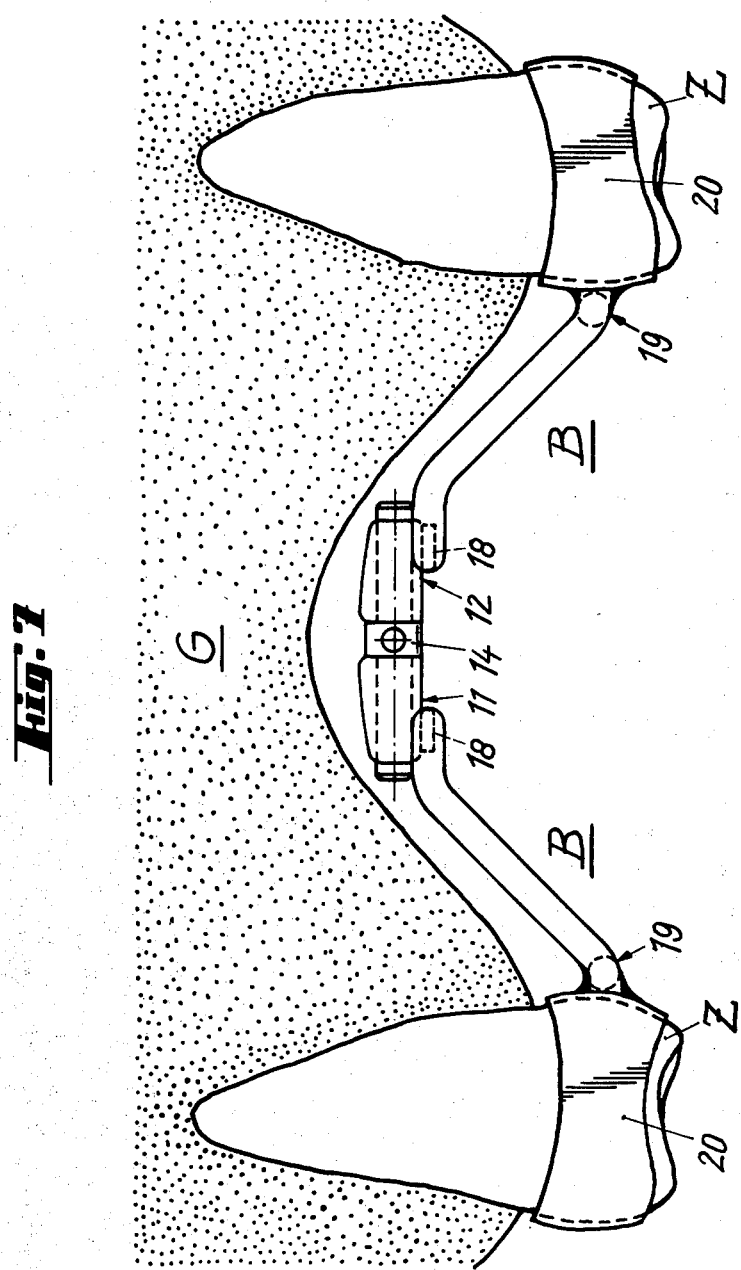

ORTHODONTIC SPREADER

BACKGROUND OF THE INVENTION

1. Field of the Invention

This invention relates to an orthodontic spreader, which comprises an actuating screw and pressure-transmitting nuts screwed on both end portions of the screw and is mainly intended for correcting the positions of molars in the upper jaw.

2. Description of Prior Art

Such orthodontic spreaders which comprise an actuating screw and pressure-transmitting nuts screwed on both end portions of the screw and are mainly intended for correcting the positions of molars in the upper jaw are known, in which said actuating screw has end portions provided with oppositely handed screw threads and is operable to move said pressure-transmitting nuts along parallel guide rods. For instance, one known jaw-expanding spreader comprises two housing members, which are adjustable by means of an actuating screw and are guided by a single pin or by two pins. Each guide pin is an interference fit in one housing member and a sliding fit in the other housing member. In that arrangement the force-fitted guide pins increase the shortest length to which the spreader can be contracted. In order to reduce that shortest length, orthodontic spreaders have been proposed, wherein a spreader can be contracted to a shorter length because a guide extension extends from the screw-threaded portion of the first housing member toward the second housing member so that the length required for the fixation of the guide pins is reduced.

SUMMARY OF THE INVENTION

It is an object of the invention to provide an orthodontic spreader in which force is applied at points which are as close as possible to the center of resistance and which has a high pressure-applying and spreading capacity and is as convenient as possible for the patient.

In an orthodontic spreader which comprises an actuating screw and pressure-transmitting nuts screwed on both end portions of the screw and is mainly intended for correcting the positions of molars in the upper jar, that object is accomplished in that the pressure-transmitting nuts are adapted to be extended from the actuating screw in mutually opposite directions, guide rods are axially slidably mounted in the pressure-transmitting nuts, and stops are provided for limiting the longitudinal movement of the guide rods relative to the pressure-transmitting nuts. This arrangement ensures that even short pressure-transmitting nuts will be guided over large lengths.

Specifically, the stops may consist of stop collars, which are provided at the ends of the guide rods and may be integrally formed therewith. These stop collars limit the outward movement of the pressure-transmitting nuts by engaging the same on an axially outwardly facing surface.

The stops carried by the guide rods and limiting the outward movement of pressure nuts. The guide rods may also co-operate with the actuating portion of the actuating screw. In that case the actuating portion of the actuating screw may be laterally enlarged and extend into annular grooves formed on the guide rods, which may have a flat on one side so that the guide rods can be assembled with the screw and can subsequently be rotated so as to be fixed in position by the enlarged actuating portion extending into the annular grooves.

BRIEF DESCRIPTION OF THE DRAWINGS

Two preferred embodiments of orthodontic spreaders according to the invention will now be described with reference to the drawings, in which FIGS. 1 and 2 are top plan views showing a first embodiment of such orthodontic spreader in contracted and extended positions, respectively, FIG. 3 is a top plan view showing that spreader in use at the teeth of the upper jaw, FIGS. 4 and 5 are, respectively, a top plan view and side elevation showing a second embodiment of the spreader and FIGS. 6 and 7 are, respectively, a top plan view and a side elevation showing the spreader of FIGS. 4 and 5 in use at the teeth of the upper jaw.

DESCRIPTION OF THE PREFERRED EMBODIMENTS

Figure 6:
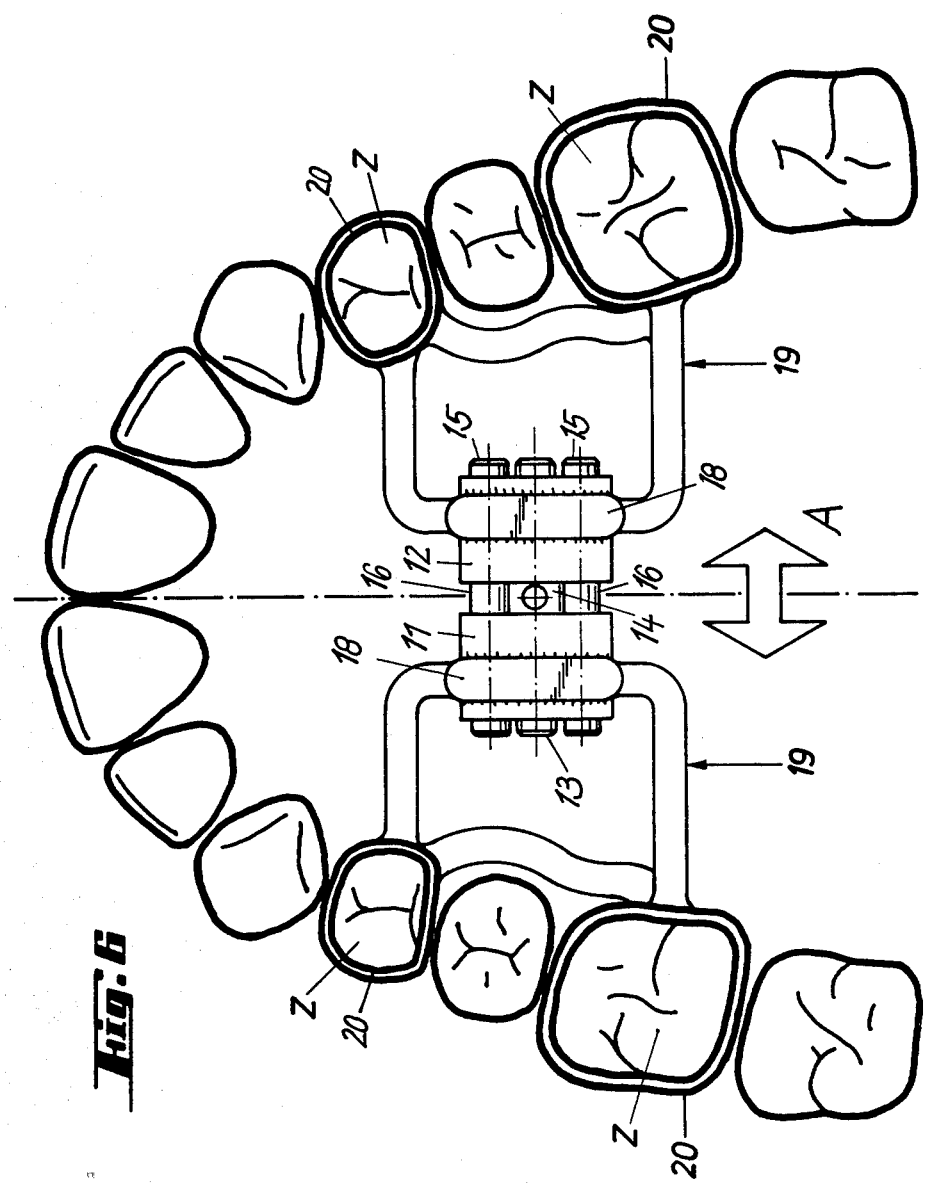

As is apparent from FIGS. 1 to 3 of the drawing, the first embodiment of the orthodontic spreader for correcting the positions of teeth of the upper jaw comprises two pressure-transmitting nuts 1, 2 screwed on an actuating screw 3 having oppositely handed end portions on opposite sides of a laterally enlarged actuating portion 4. Two parallel guide rods 5 are disposed on opposite sides of the screw 3 and are provided with stops, which limit movement of the nuts relative to the rods 5. In this embodiment these stops consist of stop collars 6, which are formed on each guide rod at opposite ends thereof and limit the outward movement of the pressure-transmitting nuts 1, 2 by engaging the latter at axially outwardly facing surfaces. In a preferred embodiment, the pressure-transmitting nuts 1, 2, are formed at their outer ends with recesses 7, which are capable of receiving the stop collars 6 to permit a further extension of the pressure-transmitting nuts. The peripheral surfaces of the recesses 7 may be provided with a plastic liner 10 as the plastic pressure-applying members 8, 9 (FIG. 3) are molded around the pressure-transmitting nuts 1 and 2, respectively. These liners 10 will present a frictional resistance to the movement of the end collars 6 of the guide rods 5 into the recesses 7. This will eliminate the gradual development of a lateral backlash, which would otherwise require the use of a new spreader. upper jaw. As shown, the spreader is mountable on a palate plate 9' having the pressure applying members 8 and 9. As can be seen, the guide rods 5 are shiftable during the installation of the pressure applying members into the plate 9'. In other words, the guide rods 5 are moved to extreme position in one direction until the stop collars 6 abut the pressure nut 1 inside its recess (not shown), as evident in FIG. 3.

As is apparent from FIGS. 4 to 7, the second embodiment of the orthodontic spreader for correcting the positions of teeth in the upper jaw also comprises two pressure-transmitting nuts 11, 12 screwed on an actuating screw 13 having oppositely handed end portions and a laterally enlarged actuating portion 14 between said end portions. Two parallel guide rods 15 are disposed on opposite sides of the screw 13. The actuating portion 14 extends into annular grooves 16 formed in the guide rods 15 so that the parts 14, 15 are held against axial movement relative to each other. To permit an assembling of the spreader, each guide rod 15 is provided with a flat 17 on one side. When the nuts 11, 12, the screw 13 and the guide rods 15 have been assembled, the guide rods 15 are rotated to interengage with the actuating portion 14 at the grooves 16, as is shown in FIG. 5.

The flats 17, as seen in FIG. 4, are facing outwardly. If the two guide rods 15 are rotated inwardly toward each other by 90°, the flats 17 will be facing each other as interposed by actuating portion 14. In this position, the actuating means 14 is free of contact with the guide rods 15. When the flats 17 occupy the position shown in FIG. 5, the actuating means 14 is in engagement with the two guide rods 15. The pressure nuts 11, 12 possess, at their exterior side, recesses 7', similar to the recesses 7 shown in FIG. 1. The guide rods 15 possess stops (not shown) similar to the stop collars 6 shown in FIG. 1. Consequently, the pressure nuts 11, 12 can move outwardly to each other by a limited distance.

An intermediate portion 18 of a pressure-applying bracket is mounted, e.g., by laser welding, on each pressure transmitting nut 11 or 12 and extends transversely to the direction A (FIG. 6) in which pressure is applied. Each of said brackets has two arms, which are bent from said intermediate portion at opposite ends thereof at right angles thereto and serve to apply pressure to the teeth Z. As is shown in FIG. 6 these arms are bent so that the bracket comprises an additional transverse member 19 for engaging the teeth. In the embodiment shown in FIG. 7 the framelike brackets 18, 19 are upwardly curved in the region B so that they generally conform to the palate G and the pressure-transmitting nuts 11 and 12 also conform somewhat to the shape of the palate G. The brackets 18, 19, are secured to the teeth Z by means of cuffs 20.

What is claimed is:

1. In an orthodontic spreader comprising
two pressure-transmitting nuts,
an actuating screw including two screw-threaded, oppositely handed end portions screwed into respective ones of said pressure-transmitting nuts, and
at least one guide rod, which is parallel to said screw and extends as a sliding fit through both said pressure-transmitting nuts,
the improvement residing in that
said actuating screw comprises an actuating portion between said screw-threaded end portions and
restraining means for axially restraining said guide rod are provided and comprise stops carried by said guide rod,
said actuating portion is laterally enlarged and
said guide rod is provided with an annular groove, said actuating portion engaging with said groove to limit the axial movement of said guide rod relative to said actuating portion.

2. The improvement set forth in claim 1 as applied to an orthodontic spreader comprising two of said guide rods.

3. The improvement set forth in claim 1, wherein said stops are engageable with said pressure-transmitting nuts to limit the axial movement of said guide rod relative to said pressure-transmitting nuts.

4. The improvement set forth in claim 3, wherein said stops consist of collars carried by said guide rod at opposite ends thereof, and each of said pressure-transmitting nuts has an axially outwardly facing surface which is engageable by one of said stop collars.

5. The improvement set forth in claim 4, wherein each of said pressure-transmitting nuts has an axially outer end face formed with a recess which is adapted to receive one of said stops.

6. The improvement set forth in claim 5, wherein each of said recesses is lined at its periphery with plastic material adapt to present a frictional resistance to the movement of the associated one of said stop collars in said recess.

7. The improvement set forth in claim 4, wherein each of said stop collars consists of an upset end portion of said guide rod.

8. The improvement as set forth in claim 4, as applied to a spreader comprising two pressure-applying members, each of which is molded around one of said pressure-transmitting nuts and engageable with the palate of a patient, wherein
said restraining means permit an axial movement of said guide rod to a position in which one of said stop collars engages said axially outwardly facing surface of one of said nuts when said nuts are as close as possible to each other.

9. The improvement set forth in claim 1, wherein each of said pressure-transmitting nuts carries at its outer end a pressure-applying bracket having an intermediate portion which is secured to said pressure-transmitting nut and which extends transversely to the axial direction of said screw, and two arms extending from said bracket at right angles to said intermediate portion.

10. The improvement set forth in claim 9, wherein said spreader is designed to be received by the palate near the palatinal split and operable to apply pressure near the center of resistance.

11. The improvement set forth in claim 9, wherein each of said brackets constitutes a frame,
one side of said frame constitutes said intermediate portion and
the opposite side of said frame is engageable with the teeth to apply pressure thereto.

12. The improvement set forth in claim 9, wherein said arms are curved upwardly toward the palate to generally conform to the palate.

13. In an orthodontic spreader comprising
two pressure-transmitting nuts,
an actuating screw including two screw-threaded, oppositely handed end portions screwed into respective ones of said pressure-transmitting nuts, and
at least one guide rod, which is parallel to said screw and extends as a sliding fit through both said pressure-transmitting nuts,
the improvement residing in that
said actuating screw comprises an actuating portion between said screw-threaded end portions,
restraining means for axially restraining said guide rod are provided and comprise stops carried by said guide rod,
said guide rod is formed on one side in a mid-portion with a flat and is formed in said mid-portion on the remainder of its periphery with a partial annular groove for receiving said actuating portion and
said guide rod has ends rotatably mounted in both said pressure-transmitting nuts.

* * * * *